(12) United States Patent
Paschen et al.

(10) Patent No.: US 9,169,519 B2
(45) Date of Patent: Oct. 27, 2015

(54) SUMO AS A MARKER OF CANCER DEVELOPMENT AND TARGET FOR CANCER THERAPY

(75) Inventors: Wulf Paschen, Durham, NC (US); Wei Yang, Cary, NC (US); Huaxin Sheng, Chapel Hill, NC (US); David S. Warner, Chapel Hill, NC (US)

(73) Assignee: Duke University, Durham, NC (US)

( * ) Notice: Subject to any disclaimer, the term of this patent is extended or adjusted under 35 U.S.C. 154(b) by 1 day.

(21) Appl. No.: 13/641,639

(22) PCT Filed: Apr. 15, 2011

(86) PCT No.: PCT/US2011/032727
§ 371 (c)(1),
(2), (4) Date: Oct. 16, 2012

(87) PCT Pub. No.: WO2011/130660
PCT Pub. Date: Oct. 20, 2011

(65) Prior Publication Data
US 2013/0046010 A1 Feb. 21, 2013

Related U.S. Application Data (60) Provisional application No. 61/325,010, filed on Apr. 16, 2010.

(51) Int. Cl.
| | |
|---|---|
| C12N 15/11 | (2006.01) |
| C12Q 1/68 | (2006.01) |
| C12N 15/113 | (2010.01) |
| G01N 33/574 | (2006.01) |

(52) U.S. Cl.
CPC ............ *C12Q 1/6886* (2013.01); *C12N 15/113* (2013.01); *G01N 33/57484* (2013.01); *C12N 2310/141* (2013.01); *C12N 2330/51* (2013.01); *C12Q 2600/112* (2013.01); *G01N 2333/4706* (2013.01); *G01N 2440/36* (2013.01); *G01N 2500/10* (2013.01); *G01N 2800/56* (2013.01)

(58) Field of Classification Search
CPC ....................................................... C12Q 1/68
See application file for complete search history.

(56) References Cited

U.S. PATENT DOCUMENTS

2002/0031818 A1* 3/2002 Ronai et al. ................... 435/226
2008/0051404 A1* 2/2008 Claiborne et al. ............ 514/245

OTHER PUBLICATIONS

Wu et al, MicroRNA-mediated Regulation of Ubc9 Expression in Cancer Cells, 2009, Clin Cancer Res, 15:1550-1557.*
Osoba et al, Health-related quality of life in patients with anaplastic astrocytoma during treatment with temozolomide, 2000, European Journal of Cancer, 36: 1788-1795.*
Katayama et al, Overexpression of small ubiquitin-related modifier-1 and sumoylated Mdm2 in oral squamous cell carcinoma: Possible involvement in tumor proliferation and prognosis, 2007, 31: 517-524.*
Bruderer et al., "Purification and identification of endogenous polySUMO conjugates," EMBO Reports 12: 142-148 (2011).
Cai et al., "Hypoxia Inactivates the VHL Tumor Suppressor through PIASy-Mediated SUMO Modification," PloS ONE 5: e9720 (2010).
Callus et al., "Cytoplasmic p53 is not required for PUMA-induced apoptosis," Cell Death Diff. 15: 213-219 (2008).
Carbia-Nagashima et al., "RSUME, a Small RWD-Containing Protein, Enhances SUMO Conjugation and Stabilizes HIF-1 rL during Hypoxia," Cell 131: 309-323 (2007).
Chen & Qi, "SUMO modification regulates the transcriptional activity of XBP1," Biochem. J. 429: 95-102 (2010).
Genbank AF002385.1.
Genbank AF046025.2.
Genbank AF077952.1.
Genbank AF079566.1.
Genbank AF090384.1.
Genbank AF090385.2.
Genbank AF110956.1.
Genbank AF110957.1.
Genbank AK315624.1.
Genbank BC000344.2.
Genbank BC003153.1.
Genbank BC003611.2.
Genbank BC018271.1.
Genbank BT007290.1.
Genbank BT009781.1.
Genbank CR456756.1.
Genbank NM_001005781.1.
Genbank NM_001005782.1.
Genbank NM_001005849.1.
Genbank NM_001145713.1.
Genbank NM_001145714.1.
Genbank NM_003334.3.
Genbank NM_004671.2.
Genbank NM_005499.2.
Genbank NM_005500.2.
Genbank NM_006099.
Genbank NM_006936.2.
Genbank NM_015897.2.
Genbank NM_03352.4.
Genbank NM_153280.2.
Genbank NM_006937.3.
Genbank NM_173206.2.
Genbank NR_027280.1.
Huang et al., "Sequential Modification of NEMO/IKK'Y by SUM0-1 and Ubiquitin Mediates NF-KB Activation by Genotoxic Stress," Cell 115: 565-576 (2003).
Kim et al., "Roles of sumoylation of a reptin chromatin-remodelling complex in cancer metastasis," Nature Cell Biol. 8: 631-639 (2006).
Kim et al., "SUMOylation of pontin chromatin-remodeling complex reveals a signal integration code in prostate cancer cells" Proc. Natl. Acad. Sci. USA 104: 20793-20798 (2007).

(Continued)

*Primary Examiner* — Tracy Vivlemore
*Assistant Examiner* — Kate Poliakova
(74) *Attorney, Agent, or Firm* — Michael Best & Friedrich LLP (57) ABSTRACT

Disclosed herein are methods relating to inhibiting or reducing proliferation of a cancer cell, for treating cancer in a subject in need of treatment, predicting the risk of progression of cancer to a more aggressive cancer, and screening for cancer in a subject, that comprise detecting and/or decreasing the levels of SUMO conjugated proteins and detecting and/or interfering with SUMO conjugation.

18 Claims, 7 Drawing Sheets

(56) References Cited

OTHER PUBLICATIONS

Krebs and Alsberg, "Localized, Targeted, and Sustained siRNA Delivery" Chem. Eur. J 17: 3054-3062 (2011).

Lee et al., "Protein SUMOylation is massively increased in hibernation torpor and is critical for the cytoprotection provided by ischemic preconditioning and hypothermia in SHSYSY cells," J. Cereb. Blood Flow Metabol. 27: 950-962 (2007).

Lee, J.Y., et al., "SUMOylation participates in induction of ischemic tolerance" J N eurochem, 2009, 109: 257-267.

Lieberman et al. "Pharmaceutical Dosage Forms: Tablets," Marcel Dekker, Inc. (1981).

Lin et al., "A robust in vivo positive-readout system for monitoring siRNA delivery to xenograft tumors," RNA 17:603-612 (2011).

Malden et al., "Selective Amplification of the Cytoplasmic Domain of the Epidermal Growth Factor Receptor Gene in Glioblastoma Multiforme," Cancer Res. 48: 2711-2714 1988.

Mann & Hendershot, "UPR Activation Alters Chemosensitivity of Tumor Cells,"Cancer Biol. Ther. 5: 736-740 (2006).

Maxwell et al., "Hypoxia-inducible factor-1 modulates gene expression in solid tumors and influences both angiogenesis and tumor growth," Proc. Natl. Acad. Sci. USA 94: 8104-8109 (1997).

Nguyen et al., "SUMOylation Attenuates Sensitivity toward Hypoxiaor Desferroxamine-lnduced Injury by Modulating Adaptive Responses in Salivary Epithelial Cells," Am. J. Pathol. 168: 1452-1463 (2006).

Parmar et al., "Ex vivo expanded umbilical cord blood T cells maintain naive phenotype and TCR diversity," Cyrorherapy (2006) vol. 8, No. 2, 149-157.

Rosas-Acosta et al., "A Universal Strategy for Proteomic Studies of SUMO and Other Ubiquitin-like Modifiers," Mol. Cell, Proteornics 4: 56-72 (2005).

Rosenberg et al., "IL-7 Administration to Humans Leads to Expansion of CD8+ and CD4+ Cells but a Relative Decrease of CD4+ T-Regulatory Cells," J lmmunother, vol. 29, No. 3, May/Jun. 2006, 313-319.

Schlegel et al., "Amplification of the Epidermal-Growth-Factor-Receptor Gene Correlates With Different Growth Behaviour in Human Glioblastoma," Int. J. Cancer. 56: 72-77 (1994).

Szabolcs et al., "Immune reconstitution after unrelated cord blood transplantation," Cyrorherapy (2007) vol. 9, No. 2, 111-122.

Vertegaal et al., "A Proteomic Study of SUM0-2 Target Proteins," J. Biol. Chem. 279: 33791-33798 (2004).

Wang & Banerjee, "Differential PIAS3 expression in human Inalignancy," Oncol. Rep. 11: 1319-1324 (2004).

Xie et al., "Constitutive NF -KB activity regulates the expression of VEGF and IL-8 and tumor angiogenesis of human glioblastoma," Oncol. Rep. 23: 725-732 (2010).

Xu et al., "Comprehensive Invited Review. SUMO Proteases: Redox Regulation and Biological Consequences" Antioxid. Redox Signal. 11: 1453-1484 (2009).

Yang, W., et al., "Deep hypothermia markedly activates the small ubiquitin-like modifier conjugation pathway; implications for the fate of cells exposed to transient deep hypothetmic cardiopulmonary bypass" J Cereb Blood Flow Metabo, 2009, 129: 886-890.

Yang, W., et al., Gene expression and cell growth are modified by silencing SUMO2 and SUMO3 expression. Biochem Biophys Res Commun, 2009, 382: 215-218.

Yang, W., et al., "Transient focal cerebral ischemia induces a dramatic activation of small ubiquitin-like modifier conjugation" J Cereb Blood Flow Metabo, 2008, 128: 892-896.

Yang, W., et al., "Transient global cerebral ischemia induces a massive increase in protein sumoylation" J Cereb Blood Flow Metabol, 2008, 28: 269-279.

Yang et al., "Deep hypothermia markedly activates the small ubiquitin-like modifier conjugation pathway; implications for the fate of cells exposed to transient deep hypothermic cardiopulmonary bypass," Journal of Cerebral Blood Flow & Metabolism (2009) 29, 886-890.

Ye, "SUMOylation and De-SUMOylation: Wrestling with Life's Processes," J. Bioli. Chern. 284: 8223-8227 (2009).

PCT/US2011/032727 International Preliminary Report on Patentability and Written Opinion dated Oct. 18, 2012 (7 pages).

\* cited by examiner

SUMO AS A MARKER OF CANCER DEVELOPMENT AND TARGET FOR CANCER THERAPY

CROSS-REFERENCE TO RELATED APPLICATIONS

This application is a national stage filing under 35 U.S.C. 371 of International Application No. PCT/US2011/032727, filed Apr. 25, 2011, which claims the benefit of priority to U.S. Provisional Patent Application Ser. No. 61/325,010, filed Apr. 16, 2010, the disclosures of each of which are incorporated by reference herein in their entireties. Priority to each application is hereby claimed.

SEQUENCE LISTING

The sequence listing is filed with the application in electronic format only and is incorporated by reference herein. The sequence listing text file "ASFILED SequenceListing" was created on May 5, 2011, and is 845 bytes in size.

BACKGROUND

Astrocytomas, brain tumors originating from differentiated astrocytes, show a tendency for progression towards a more malignant phenotype. Astrocytomas are classified, according to the WHO malignancy scale, into low-grade astrocytoma (WHO Grade II; "AII"), anaplastic astrocytoma (WHO Grade III; "AIII"), and glioblastoma multiforme (WHO Grade IV; "GBM"). GBM, the most common form of primary brain tumor, carries a very poor prognosis even after surgical resection with subsequent radio- and chemotherapy.

Small ubiquitin-like modifier (SUMO) proteins are a group of small proteins that bind lysine residues of target proteins and thereby modify target protein activity, stability, and subcellular localization. SUMO2 and SUMO3 proteins share a high degree of similarity (95% sequence identity), but are relatively distinct from SUMO1 (only 50% sequence identity). Like ubiquitin, SUMO protein is synthesized as a larger precursor protein that is processed by sentrin-specific proteases (SENPs) to expose the two C-terminal glycine residues that provide for conjugation. SUMO conjugation (or "sumoylation") is a highly volatile process, with various enzymes involved in the conjugation, e.g., E1, E2 and Ubc9, and de-conjugating (or "de-sumoylation") e.g., SENPs, processes. A large portion of SUMO conjugation targets transcription factors and other nuclear proteins involved in gene expression. A major change in levels of SUMO conjugated proteins may have a major impact on the fate of cells.

SUMMARY

In an aspect the disclosure relates to a method of treating cancer in a subject in need of treatment, comprising administering to the subject an effective amount of an agent that causes levels of SUMO conjugated proteins to decrease, wherein the cancer comprises cells having increased level of expression or conjugation, or both, of at least one member of the SUMO conjugation pathway relative to control cells.

In an aspect, the disclosure relates to a method of screening for a cancer in a subject comprising detecting the level of expression or conjugation, or both, of at least one member of the SUMO conjugation pathway in a sample from the subject and comparing the level of expression or conjugation, or both, to a level of expression or conjugation, or both, of the same member of the SUMO conjugation pathway in a control, wherein an increased level of expression or conjugation, or both, of the member of the SUMO conjugation pathway identifies the subject as at risk of having cancer.

In an aspect, the disclosure relates to a method of predicting the risk of progression of a cancer to a more aggressive type of cancer, comprising detecting the level of expression or conjugation, or both, of at least one member of the SUMO conjugation pathway in the cancer cell and comparing the level of expression or conjugation, or both, of the at least one member of the SUMO conjugation pathway to a control cell.

In another aspect, the disclosure relates to a method of assessing an agent for chemotherapeutic potential, comprising contacting a cell with the agent and evaluating the level of expression or conjugation, or both, of at least one member of the SUMO conjugation pathway in the contacted cell, a decrease in the level of expression or conjugation, or both, of the SUMO conjugation pathway in the contacted cell identifies the agent as having chemotherapeutic potential.

In an aspect, the disclosure relates to a method of reducing proliferation of a cancer cell comprising contacting the cancer cell with an agent that causes levels of SUMO conjugated proteins to decrease in an amount effective to reduce proliferation, wherein the cancer cell is associated with an increased level of expression at least one member of the SUMO conjugation pathway or an increased level of SUMO conjugated proteins, or both, relative to a control cell.

In an aspect, the disclosure relates to a method of promoting differentiation of a cancer cell comprising contacting the cell with an agent that causes levels of SUMO conjugated proteins to decrease in an amount effective to increase differentiation, wherein the cancer cell is associated with an increased level of expression or conjugation, or both, of at least one member of the SUMO conjugation pathway relative to a control cell.

In an aspect, the disclosure relates to a method of inhibiting the survival of a cancer cell comprising contacting the cell with an effective amount of an agent that causes levels of SUMO conjugated proteins to decrease in an amount effective to inhibit survival of the cell.

In an aspect, the disclosure relates to a method of inhibiting DNA synthesis in a cancer cell comprising contacting the cell with an amount of an agent that causes levels of SUMO conjugated proteins to decrease and an amount of TMZ or radiation effective to inhibit DNA synthesis, wherein the cancer cell is associated with an increased level of expression or conjugation, or both, of at least one member of the SUMO conjugation pathway relative to a control cell.

In an aspect, the disclosure relates to a method of inducing cell death in a cancer cell comprising contacting the cell with a combination of an amount of an agent that causes levels of SUMO conjugated proteins to decrease and an amount of TMZ or radiation effective to induce cell death, wherein the cancer cell is associated with an increased level of expression or conjugation, or both, of at least one member of the SUMO conjugation pathway relative to a control cell.

Aspects of the disclosure relate to methods of adjuvant therapy. In some of these aspects, the disclosure provides a method of sensitizing a cancer cell to a therapeutic regimen comprising contacting the cancer cell with an agent in an amount effective to inhibit SUMO conjugation in the cancer cell.

Other aspects and embodiments are encompassed by the disclosure and will become apparent in light of the following description and accompanying drawings.

DETAILED DESCRIPTION

Before any aspects and embodiments are explained in detail, it is to be understood that the disclosure is not limited in its application to the details of construction and the arrangement of components set forth in the following description or illustrated in the Drawings. One of skill in the art will be able to envision other aspects and embodiments and will appreciate that the methods described herein can be practiced or carried out in alternative ways.

In a general sense, the disclosure relates to biochemical pathways and methods for treating cancer or inhibiting tumor growth, such as brain tumors. The inventors have found that the SUMO conjugation pathway is activated in cancers such as, for example, astrocytomas (e.g., glioblastoma multiforme). For example, as described herein, the levels of SUMO1 and SUMO2/3 conjugated proteins are elevated (i.e., increased) in human astrocytomas as compared to surrounding normal brain tissues and correlate to the malignancy grade of the astrocytoma. Current strategies for therapeutic treatment of many cancers, such as brain cancer, typically focus on modulation of targeted proteins that have elevated expression or activity; yet no targeted protein or pathway has been effective in all types or subtypes of brain cancer (e.g., GBM). EGFR, for example, is typically over-expressed in about 40-60% of GBM samples. The methods disclosed herein provide an alternative strategy for combating cancer (e.g., inhibiting and/or preventing survival, growth, and/or proliferation of cancer cells) because SUMO conjugation plays a role in various cellular processes and pathways, targeting various proteins/pathways integral to underlying pathological processes.

Thus, in an aspect the disclosure relates to treating cancer in a subject in need of treatment, comprising administering to the subject an effective amount of an agent that causes levels or amounts of SUMO conjugated proteins to decrease, wherein the cancer comprises cells having increased level of expression or conjugation, or both, of at least one member of the SUMO conjugation pathway relative to control cells. In embodiments, the agent causes levels or amounts of SUMO conjugated proteins to decrease in a cell when the cell is contacted with the agent directly or indirectly in vivo, in vitro or ex vivo. In embodiments, the method further comprises administering a second anti-cancer therapy to the subject. In embodiments, the second anti-cancer therapy may be an effective amount of chemotherapy or radiation therapy. In embodiments, the chemotherapy may be temozolomide ("TMZ"), Camptosar (Irinotecan), Carmustine (BCNU), Lomustine (CCNU), Methotrexate, Polifeprosan 20 with carmustine implant, Procarbazine (Matulane), Thalidomide, and Vincristine.

Radiation useful in the methods includes but is not limited to, X-rays, gamma rays, radioactive seeds and radionuclides. Radiation may be administered externally or internally using conventional radiation dosing schedules. For example, radiation therapy may be given daily, 5 days per week. In embodiments, the radiation therapy includes a gamma knife radiosurgery. Radiation dosage depends on a number of factors including tumor type, age, weight and condition of the patient, as well as other factors typically considered by the skilled clinician. In embodiments, the radiation dosage may range from 1-10 Gy. The total dose can be given in daily fractions using external beam radiation. It is envisioned that administration of an agent that causes levels or amounts of SUMO conjugated proteins to decrease, in combination with radiation will result in increased cellular effects for given dose of radiation. Alternatively, lower dosages of radiation may be employed when used in combination with agent that causes levels or amounts of SUMO conjugated proteins to decrease than are typically used in radiation therapy alone.

In embodiments, the agent is an inhibitor of at least one member of the SUMO conjugation pathway. In embodiments, a member of the SUMO conjugation pathway includes but is not limited to proteins that can conjugate and/or can be conjugated to at least one of SUMO1, SUMO2, and SUMO3, proteins. In embodiments, a member of the SUMO conjugation pathway includes proteins and enzymes that are specific to the SUMO conjugating or de-conjugating processes. In the embodiments described herein, a member of the SUMO conjugation pathway includes SUMO1, SUMO2 or SUMO3, activating enzymes (E1), the conjugating enzyme Ubc9 (E2), ligating enzymes (E3; Ye, *J. Biol. Chem.* 284: 8223-8227 (2009)), and/or deconjugating enzymes (SENPs; Xu et al., *Antioxid. Redox Signal.* 11: 1453-1484 (2009)). Other members of the SUMO conjugation pathway include RWD-containing sumoylation enhancer (RSUME) (Carbia-Nagashima et al., *Cell* 131: 309-323 (2007)) and SUMO E3 ligase PIASy (Wang & Banerjee, *Oncol. Rep.* 11: 1319-1324 (2004)). Some embodiments relate to a target protein of the SUMO conjugation pathway and include, for example, HIF-1α (Carbia-Nagashima et al., *Cell* 131: 309-323 (2007)), UPR (Mann & Hendershot, *Cancer Biol. Ther.* 5: 736-740 (2006)), XBP1, (Chen & Qi, *Biochem. J.* 429: 95-102 (2010)), NF-kappaB (Xie et al., *Oncol. Rep.* 23: 725-732 (2010)), VEGF (Xie et al., *Oncol. Rep.* 23: 725-732 (2010)), IL-8 (Xie et al., *Oncol. Rep.* 23: 725-732 (2010)), NF-kappaB essential modifier (Huang et al., *Cell* 115: 565-576 (2003)), proteins involved in cellular proliferation, invasion, angiogenesis and stress response pathways, the von Hippel Lindau (VHL) tumor suppressor (Cai et al., *PloS ONE* 5: e9720 (2010)), reptin and pontin, (Kim et al., *Nature Cell Biol.* 8: 631-639 (2006); Kim et al., *Proc. Natl. Acad. Sci. USA* 104: 20793-20798 (2007)). In some embodiments, targets of SUMO conjugation include various other transcription factors and other nuclear proteins involved in gene expression and genomic integrity (Vertegaal et al., *J. Biol. Chem.* 279: 33791-33798 (2004); Rosas-Acosta et al., *Mol. Cell, Proteomics* 4: 56-72 (2005); Bruderer et al., *EMBO J.* 12: 142-148 (2011)).

In embodiments, the inhibitor of the member of the SUMO conjugation pathway is an inhibitory RNA. An inhibitory RNA may be a sequence complementary to a portion of an RNA sequence encoding SUMO. In embodiments, an inhibitory RNA may refer to, but is not limited to dsRNA, siRNA, shRNA, miRNA, piRNA, RNAse external guide sequences, ribozymes, and other short catalytic RNAs. In embodiments, the inhibitory RNA comprises a miRNA comprising a sequence complementary to a sequence of Ubc9, SUMO1, SUMO2, or SUMO3, or any combination thereof. In embodiments, the RNA sequence encoding the member of the SUMO conjugation pathway, i.e., SUMO1-3, SUMO activating, conjugating and ligating enzymes, is selected from any of GenBank Accession Nos. NM_001005781.1, NM_001005782.1, NM_03352.4 (SUMO1); NM_001005849.1, NM_006937.3 (SUMO2); NM_006936.2 (SUMO3); AF002385.1 (Ubc9); NM_006099 (SUMO ligating enzyme PIAS3); NM_173206.2, NM_004671.2 (SUMO ligating enzyme PIAS2); NM_015897.2 (SUMO ligating enzyme PIAS4); AF077952.1 (SUMO ligating enzyme PIASy); NM_001145713.1, NM_005500.2, NM_001145714.1, NM_003334.3, NM_153280.2, NM_005499.2, NR_027280.1, AF110956.1, AF110957.1, AF079566.1, AF090384.1, AF090385.2, AF046025.2, BC003611.2, BC000344.2, BC018271.1, BC003153.1, BT009781.1, BT007290.1, CR456756.1, and AK315624.1. In embodiment, the inhibitory RNA may be one of SEQ ID NOs: 1-3. Methods of synthesis, design and delivery of inhibitory RNA are well known in the art, see, e.g., Integrated DNA Technologies, Inc. "Dicer Substrate RNAi Design" at the idtdna.com site; Krebs and Alsberg, *Chem. Eur. J.* 17: 3054-3062 (2011); Lin et al., *RNA* 17:603-612 (2011).

In embodiments, the agent is an activator of SUMO deconjugation. In embodiments, the agent is an activator of at least one member of the SENPs. In embodiments, a member of the SENPs includes but not limited to deconjugating enzymes (SENPs; Xu et al., *Antioxid. Redox Signal.* 11: 1453-1484 (2009)). In embodiments, the member of the SENPs desumoylate SUMO conjugated proteins.

In embodiments, the sample can be any type of biological sample derived from the subject such as, for example, blood, cerebrospinal fluid, urine, saliva, a tissue biopsy, and tumor cells.

In embodiments, the cancer can comprise sarcoma, carcinoma, lymphoma, glioblastoma, or astrocytoma. In embodiments, the cancer is brain cancer. As used herein, "brain cancer" refers to any form of cancer that affects the brain or central nervous system such as, for example, infiltrative astrocytoma, pilocytic astrocytoma, oligodendroglioma, mixed oligoastrocytoma, GBM, ependymoma, medulloblastoma, meningioma, acoustic neuroma, lymphoma, penial gland tumor, pituitary adenoma, and schwannoma. The cancer can be of any severity grade such as WHO Grade I, WHO Grade II (e.g., low-grade astrocytoma), WHO Grade III (e.g., anaplastic astrocytoma), and WHO Grade IV (e.g., glioblastoma multiforme). In embodiments, the cancer is selected from astrocytomas including low-grade astrocytoma, anaplastic astrocytoma, and GBM. In some embodiments, the cancer is GBM.

As used herein, "expression levels" refers to a measure of the production of a biological product encoded by a nucleic acid sequence, such as gene sequence and typically refers to the relative or absolute amount or activity of the gene product. This biological product, referred to herein as a "gene product," may be a nucleic acid or a polypeptide. The nucleic acid is typically an RNA molecule which is produced as a transcript from the gene sequence. The RNA molecule can be any type of RNA molecule, whether either before (e.g., precursor RNA) or after (e.g., mRNA) post-transcriptional processing. cDNA prepared from the mRNA of a sample is also considered a gene product. A polypeptide gene product is typically a peptide or protein that is encoded by the coding region of the gene, and is produced during mRNA translation. In embodiments, the expression levels may refer to reduced expression. In some embodiments, the expression levels may refer to increased expression.

In embodiments, the increased level of expression of the member of the SUMO conjugation pathway may be indicated by an increase in the RNA levels of SUMO1, SUMO2 or SUMO3, an increase in the amount of conjugated SUMO1, SUMO2 or SUMO3, an increase in the amount of free SUMO1, SUMO2 or SUMO3, or a combination thereof. In embodiments, SUMO is at least one of SUMO1, SUMO2, and SUMO3. The level of expression of a member of the SUMO conjugation pathway in the cancer cell may be evaluated by a variety of techniques, as will be appreciated by one of skill in the art. For example, the level of expression of a member of the SUMO conjugation pathway may be evaluated by detecting the presence and/or quantifying the amount of protein or mRNA using techniques including, but not limited to, Western blot, ELISA, Northern blot, real time PCR, immunofluorescence, or FACS analysis. The expression of a member of the SUMO conjugation pathway may be evaluated by immunofluorescence by visualizing cells stained with a fluorescently-labeled SUMO-specific antibody, Western blot analysis of SUMO protein expression, and RT-PCR of SUMO transcripts. The expression of the SUMO conjugation pathway may be evaluated by microarray analysis.

In embodiments, SUMO conjugation can be determined by measuring mRNA or protein levels of at least one member of the SUMO conjugation pathway. SUMO conjugation can be determined by measuring the activity of SUMO conjugation of a target protein. The activity of SUMO conjugation can be determined by isolating the components of the SUMO conjugation pathway from tissue samples, adding SUMO1, SUMO2 or SUMO3, ATP, an ATP regenerating system, and a SUMO conjugation target protein, and analyzing the results of the reaction by Western blotting using an antibody directed against the target protein. The activity of SUMO conjugation of the target protein can then be identified by the appearance of higher molecular weight bands that disappear after incubation with SENP. SUMO deconjugation can be measured using extracts from tissue containing tissue SENPs, adding a SUMO conjugated protein such as polySUMO and measuring deconjugation by Western blotting (polySUMO deconjugated to monoSUMO), similar to the analysis for conjugation. In embodiments, SUMO conjugation of transcription factors involved in tumor development is determined by transfecting tumor cells with a construct that will silence the expression of endogenous transcription factor and also express a mutated transcription factor that cannot be SUMO conjugated, and evaluate the effect of mutation on target gene expression.

The level of expression of the member of the SUMO conjugation pathway may be compared to a control or reference. A control or reference may include, for example, the level of expression of the member of the SUMO conjugation pathway in a control cell or reference cell, such as a non-cancerous cell, optionally from a similar type, or the same type, of tissue as the sample. A non-cancerous cell may include peritumoral gray or white matter samples or any other cell type in the brain that can de-differentiate to a cancer cell. A control may include an average range of the level of expression of the SUMO conjugation pathway from a population of non-cancer cells, or alternatively, a standard value developed by analyzing the results of a population of non-cancer cells. A control or reference may include, for example, the level of expression of the member of the SUMO conjugation pathway in an untreated sample of tissue of similar type, or the same type as the sample contacted with an agent. Those skilled in the art will appreciate that a variety of controls or references may be used.

In an aspect, the disclosure relates to a method of screening for cancer in a subject comprising detecting the level of expression and/or conjugation of at least one member of the SUMO conjugation pathway in a sample from the subject and comparing the level of expression and/or conjugation of the at least one member of the SUMO conjugation pathway to the level of expression and/or conjugation of the same member of the SUMO conjugation pathway in a control, wherein an increased level of expression and/or conjugation of the member of the SUMO conjugation pathway identifies the subject as at risk of having cancer.

In an aspect the disclosure provides a method for treating a mammalian subject having cancer, wherein the cancer has increased expression of at least one member of the SUMO conjugation pathway relative to a reference, comprising administering to the subject an effective amount of agent capable of decreasing expression and/or conjugation of at least one member of the SUMO conjugation pathway. In embodiments, an effective amount of agent is capable of decreasing expression and/or conjugation of at least one member of the SUMO conjugation pathway. In embodiments, an effective amount of agent is capable of decreasing the amount of SUMO conjugation. The reference may include a control cell, such as a non-cancer cell of the same type as the cancer cell or a standard based on such a control cell, as described above.

As used herein, the term "treat" or "treating" a subject having a disorder (e.g., cancer) refers to administering a regimen to the subject, e.g., the administration of a combination of an agent capable of decreasing expression and/or conjugation of at least one member of the SUMO conjugation pathway, such that at least one symptom of the disorder is cured, healed, alleviated, relieved, altered, remedied, ameliorated, or improved. Treating includes administering an amount effective to alleviate, relieve, alter, remedy, ameliorate, improve or affect the disorder or the symptoms of the disorder. The treatment may inhibit deterioration or worsening of a symptom of a disorder (i.e., inhibiting or slowing progression of the disease or associated symptom/clinical indication).

In an aspect the disclosure provides a method of assessing an agent for chemotherapeutic potential, comprising contacting a cell with the agent and evaluating the level of expression of at least one member of the SUMO conjugation pathway in the contacted cell, wherein a decrease in the level of expression of the SUMO conjugation pathway in the contacted cell relative to an untreated cell identifies the chemotherapeutic potential of the agent. A control or reference may include comparison to the level of expression of at least one member of the SUMO conjugation pathway in a control or reference cell, such as a non-cancerous cell or a cancer cell with known responsiveness to a therapeutic. Alternatively, a standard value developed by analyzing the results of a population of non-cancer cells or cancer cells with known responsivities to a therapeutic may be used.

Reducing the level of expression of at least one member of the SUMO conjugation pathway in a cancer cell may reduce cancer cell survival by at least about 5%, at least about 10%, at least about 20%, at least about 30%, at least about 40%, at least about 50%, at least about 60%, or at least about 70%. A reduction in cancer cell survival may be achieved by reducing expression of at least one member of the SUMO conjugation pathway by about 50%, 40%, 30%, 20%, 10%, 5% or less as compared to the expression of the SUMO conjugation pathway prior to treatment with the agent. A reduction in cancer cell survival may be achieved by reducing expression of at least one member of the SUMO conjugation pathway by about 50%, 40%, 30%, 20%, 10%, 5% or less as compared to the expression of the SUMO conjugation pathway in a cancer cell not treated with the agent.

In some embodiments, an agent capable of decreasing the level of expression of the SUMO conjugation pathway may include an agent capable of decreasing SUMO mRNA transcripts or protein levels in the cell contacted with the agent. In one embodiment, the agent capable of decreasing the level of expression of the SUMO conjugation pathway may comprise an inhibitory RNA. An inhibitory RNA may be a sequence complementary to a portion of an RNA sequence encoding SUMO. In embodiments, an inhibitory RNA may refer to, but is not limited to dsRNA, siRNA, shRNA, miRNA, piRNA, antisense RNA, RNAse external guide sequences, ribozymes, and other short catalytic RNAs. In embodiments, the RNA sequence encoding the member of the SUMO conjugation pathway, i.e., SUMO1-3, SUMO activating, conjugating and ligating enzymes, is selected from any of GenBank Accession Nos. NM_001005781.1, NM_001005782.1, NM_03352.4 (SUMO1); NM_001005849.1, NM006937.3 (SUMO2); NM_006936.2 (SUMO3); AF002385.1 (Ubc9); NM_006099 (SUMO ligating enzyme PIAS3); NM173206.2, NM_004671.2 (SUMO ligating enzyme PIAS2); NM_015897.2 (SUMO ligating enzyme PIAS4); AF077952.1 (SUMO ligating enzyme PIASy); NM_001145713.1, NM_005500.2, NM_001145714.1, NM_003334.3, NM_153280.2, NM_005499.2, NR_027280.1, AF110956.1, AF110957.1, AF079566.1, AF090384.1, AF090385.2, AF046025.2, BC003611.2, BC000344.2, BC018271.1, BC003153.1, BT009781.1, BT007290.1, CR456756.1, and AK315624.1. In embodiment, the inhibitory RNA may be any one of SEQ ID NOs: 1-3, or any combination thereof. Methods of synthesis, design and delivery of inhibitory RNA are well known in the art, see, e.g., Integrated DNA Technologies, Inc. "Dicer Substrate RNAi Design" at the idtdna.com site; Krebs and Alsberg, *Chem. Eur. J.* 17: 3054-3062 (2011); Lin et al., *RNA* 17:603-612 (2011).

In some embodiments, the agent capable of decreasing the level of expression and/or conjugation of at least one member of the SUMO conjugation pathway may include a gene expression repressor. The agent capable of decreasing the level of expression and/or conjugation of at least one member of the SUMO conjugation pathway may also include agents that bind to the member of the SUMO conjugation pathway directly or indirectly and decrease the effective level or activity of the member, for example, by inhibiting the binding or other activity of SUMO1, SUMO2 or SUMO3. The agent capable of decreasing the level of expression and/or conjugation of at least one member of the SUMO conjugation pathway may also include agents that decrease free SUMO1, SUMO2 or SUMO3 levels or increase free SUMO1, SUMO2, or SUMO3 levels.

Cells such as, for example, one or more cancer cells as described herein, may be contacted with an agent directly or indirectly in vivo, in vitro, or ex vivo. Contacting encompasses administration to a cell, tissue, mammal, patient, or human. Further, contacting a cell includes adding an agent to a cell culture. Other suitable methods may include introducing or administering an agent to a cell, tissue, mammal, or patient using appropriate procedures and routes of administration.

In an aspect the disclosure provides a method of reducing proliferation of a cancer cell comprising contacting the cancel cell with an agent that causes levels or amounts of SUMO conjugated proteins to decrease in an amount effect to reduce proliferation, wherein the cancer cell is associated with an increased level of expression or conjugation, or both, of at least one member of the SUMO conjugation pathway relative to a control cell. In an aspect the disclosure provides a method of promoting differentiation of a cancer cell comprising contacting the cancel cell with an agent that causes levels or amounts of SUMO conjugated proteins to decrease in an amount effect to increase differentiation, wherein the cancer cell is associated with an increased level of expression or conjugation, or both, of at least one member of the SUMO conjugation pathway relative to a control cell. In embodiments, the method comprises contacting the cell with an agent capable of decreasing the level of expression or conjugation, or both, of at least one member of the SUMO conjugation pathway to reduce proliferation or increase differentiation of the cancer cell.

In another aspect, the disclosure provides a method of predicting the risk of progression of a cancer to a more aggressive type of cancer, comprising detecting the level of expression or conjugation, or both, of the at least one member of the SUMO conjugation pathway to a control cell. A control or reference may include comparison to the level of expression or conjugation, or both, of at least one member of the SUMO conjugation pathway in a control or reference cell, such as a non-cancerous cell, or a cancer cell known to be aggressive, as described above. In embodiments, an increased level of expression or conjugation, or both, of at least one member of the SUMO conjugation pathway relative to a control cell may identify the cancer cell as being at risk for progressing to a more aggressive form. In embodiments, the reference is a non-cancerous cell. In embodiments, an unchanged or similar level of expression or conjugation, or both, of at least one member of the SUMO conjugation pathway relative to the level of expression or conjugation, or both, of the member in a reference may identify the cancer cell as being at risk for progressing to a more aggressive form. In embodiments the reference is a cancer cell known to be aggressive.

Predicting may include using the information discussed above or generated by another entity to generate predictions. Predictions may be based on a comparison internal to a single assay or by comparison to a standard. For example the level of expression or conjugation, or both, of at least one member of the SUMO conjugation pathway may be used to predict a cancer's responsiveness to a therapeutic. Predictions may be generated in relation to a standard or control as discussed above. This does not mean that the predicted event will occur with 100% certainty. Predicting and prediction also includes, but is not limited to, generating a statistically based indication of whether a particular event will occur, e.g. whether the cancer will be responsive to treatment with a cancer therapeutic.

In an aspect, the disclosure relates to a method of inhibiting the survival of a cancer cell comprising contacting the cell with an effective amount of an agent that causes levels or amounts of SUMO conjugated proteins to decrease in an amount effective to inhibit survival of the cell. In embodiments, the method further comprises contacting the cancer cell with an anti-cancer agent such as a chemotherapeutic and/or radiation. In embodiments, the chemotherapeutic is TMZ.

In an aspect, the disclosure relates to a method of inhibiting DNA synthesis in a cancer cell comprising contacting the cell an amount of an agent that causes levels or amounts of SUMO conjugated proteins to decrease and an amount of TMZ or radiation effective to inhibit DNA synthesis, wherein the cancer cell is associated with increased level of expression or conjugation, or both, of at least one member of the SUMO conjugation pathway relative to a control cell.

In an aspect, the disclosure relates to a method of inducing cell death in a cancer cell comprising contacting the cell with a combination of an amount of an agent that causes levels or amounts of SUMO conjugated proteins to decrease and an amount of TMZ or radiation effective to induce cell death, wherein the cancer cell is associated with an increased level of expression or conjugation, or both, of at least one member of the SUMO conjugation pathway relative to a control cell.

In an aspect, the disclosure relates to a method of inducing cell death in a cancer cell having increased expression levels of at least one member of the SUMO conjugation pathway comprising contacting the cell with an effective amount of an inhibitor of at least one member of the SUMO conjugation pathway and contacting the cell with an effective amount of radiation, wherein the inhibitor of the member of the SUMO conjugation pathway and radiation have a synergistic effect on inducing cell death.

In embodiments, the inhibitor of at least one member of the SUMO conjugation pathway and TMZ has a synergistic effect on a cancer cell having increased expression levels of at least one member of the SUMO conjugation. In embodiments, the inhibitor of at least one member of the SUMO conjugation pathway and radiation has a synergistic effect on a cancer cell having increased expression levels of at least one member of the SUMO conjugation. The effect on a cancer cell having increased expression levels of at least one member of the SUMO conjugation pathway may include but not limited to inhibiting the growth of the cell, inhibiting DNA synthesis in the cell, inducing cell death of the cell.

The enhancement of the radiation response may lower the effective amount of radiation that exerts cellular effects or it may increase the radiation responsiveness of the cell and result in increased cellular effects of the radiation treatment. Cellular effects may include, but are not limited to, one or more of increased apoptosis of cells, increased cell death, increased inhibition of cell growth, reduced tumor volume, reduced tumor burden, clearance of a tumor, inhibition of tumor growth or tumor cell proliferation, inhibition of metastases, reduced metastases and enhanced survival of a subject bearing tumor or cancer cells having increased expression of at least one member of the SUMO conjugation pathway. "Synergistic cellular effects" indicates that the total cellular effect of the combination of an inhibitor of at least one member of the SUMO conjugation pathway and radiation is greater than the sum of the individual cellular effects of the inhibitor of at least one member of the SUMO conjugation pathway alone and radiation alone.

An effective amount or "amount effective" of an agent that causes levels or amounts of SUMO conjugated proteins to decrease refers to a sufficient amount of an agent or a compound to reduce the amount of SUMO conjugation. The result can be reduction and/or alleviation of the signs, clinical indications or symptoms, or causes of a disease, or any other desired alteration of a biological system. Accordingly, methods of treatment as disclosed herein can slow or halt the progression of a cancer. An appropriate "effective" amount in any individual case may be determined using techniques, such as a dose escalation study. Suitably, an effective amount of radiation is used in combination with the agent that causes levels or amounts of SUMO conjugated proteins to decrease. One of skill in the art will understand that the effective amount of the agent that causes levels or amounts of SUMO conjugated proteins to decrease and radiation may be inversely related, i.e., if a high dosage of agent that causes levels or amounts of SUMO conjugated proteins to decrease is used, it may be combined with a lower dose of radiation to achieve cellular effects. Alternatively, the maximum tolerated dose of the agent that causes levels or amounts of SUMO conjugated proteins to decrease, the radiation, or both the agent that causes levels or amounts of SUMO conjugated proteins to decrease and the radiation may be used to achieve greater cellular effects. Suitably, a synergistically effective combination of the inhibitor of at least one member of the SUMO conjugation pathway and radiation may be used.

A synergistically effective combination of an inhibitor of at least one member of the SUMO conjugation pathway and radiation or chemotherapeutic is a combination that gives a cellular effect, which may be therapeutic, that is greater than the sum of the cellular effects of the inhibitor of at least one member of the SUMO conjugation pathway alone and radiation/chemotherapy alone.

Aspects of the disclosure relate to methods of adjuvant therapy. In some of these aspects, the disclosure provides a method of sensitizing a cancer cell to a therapeutic regimen comprising contacting the cancer cell with an agent that causes levels or amounts of SUMO conjugated proteins to decrease in an amount effective to cause the levels of SUMO conjugated protein to decrease in the cancer cell. In some of these aspects, the disclosure provides a method of sensitizing a cancer cell to a therapeutic regimen comprising contacting the cancer cell with an inhibitor of at least one member of the SUMO conjugation pathway in an amount effective to inhibit the member of the SUMO conjugation pathway and cause the levels of SUMO conjugated protein to decrease in the cancer cell. In some of these aspects, the disclosure provides a method of sensitizing a cancer cell to a therapeutic regimen comprising contacting the cancer cell with an activator of at least one member of the SENPs in an amount effective to activate at least one member of the SENPs and cause the levels of SUMO conjugated protein to decrease in the cancer cell. In some of these aspects, the disclosure provides a method of sensitizing a cancer cell to a therapeutic regimen comprising contacting the cancer cell with an agent in an amount effective to cause the levels of SUMO conjugated proteins to decrease in the cancer cell. In some embodiments, the method of treatment can use an adjuvant therapy (i.e., additional treatment) such as, for example, when an agent that causes levels or amounts of SUMO conjugated proteins to decrease, or pharmaceutical compositions thereof, is administered after surgery or other treatments (e.g., radiation or chemotherapy such as TMZ). Accordingly, in such embodiments, the method of adjuvant therapy encompasses administering an agent that causes levels or amounts of SUMO conjugated proteins to decrease to a subject following a primary or initial treatment, and can be administered either alone or in combination with one or more other adjuvant treatments, including, for example surgery, radiation therapy, or systemic therapy (e.g., chemotherapy, immunotherapy, hormone therapy, or biological response modifiers). Those of skill in the art will be able to use statistical evidence to assess the risk of disease relapse before deciding on the specific adjuvant therapy. The aim of adjuvant treatment is to improve cancer-specific and overall survival. Because the treatment is essentially for a risk, rather than for provable cancer, it is accepted that a proportion of patients who receive adjuvant therapy will already have been effectively treated or cured by their primary surgery. Adjuvant therapy is often given following surgery for many types of cancer including, for example, colon cancer, brain cancer, head and neck cancer, lung cancer, pancreatic cancer, breast cancer, prostate cancer, and some gynecological cancers.

In certain embodiments, agents that cause levels of SUMO conjugated proteins to decrease are administered in a pharmaceutically acceptable composition, such as in or with a pharmaceutically acceptable carrier. In such embodiments, pharmaceutical compositions can be formulated in a conventional manner using one or more physiologically acceptable carriers or excipients.

As used herein, a "subject in need of treatment" refers to a subject having been diagnosed with a cancer, e.g., a brain cancer. A subject can also be one who has been determined as likely to develop a cancer such as, for example, a subject having a form of a gene indicating susceptibility of developing cancer, or a subject in whose family the cancer is more frequent than normal. Symptoms, diagnostic tests, and prognostic tests for each of the above-mentioned conditions are described in, e.g., the *Diagnostic and Statistical Manual of Mental Disorders*, $4^{th}$ ed., 1994, Am. Psych. Assoc.; and *Harrison's Principles of Internal Medicine©*," 16th ed., 2004, The McGraw-Hill Companies, Inc. In embodiments a subject can include human and non-human animals. Exemplary human subjects include a human patient having a cancer or a condition or disorder associated with a cancer as described herein, or a normal subject. The term "non-human animals" includes all vertebrates, e.g., non-mammals (such as chickens, amphibians, reptiles) and mammals, such as non-human primates, domesticated and/or agriculturally useful animals (such as sheep, dogs, cats, cows, pigs, etc.), and rodents (such as mice, rats, hamsters, guinea pigs, etc.).

"Pharmaceutically acceptable" means suitable for use in a human or other mammal. The terms "pharmaceutically acceptable carriers" and "pharmaceutically acceptable excipients" are used interchangeably and refer to substances that are useful for the preparation of a pharmaceutically acceptable composition. In certain embodiments, pharmaceutically acceptable carriers are generally compatible with the other ingredients of the composition, not deleterious to the recipient, and/or neither biologically nor otherwise undesirable.

Embodiments provide for pharmaceutically acceptable carriers including, but not limited to, substances useful for topical, intrathecal, ocular, parenteral, intravenous, intraperitoneal intramuscular, sublingual, nasal and oral administration. "Pharmaceutically acceptable carrier" also includes agents for preparation of aqueous dispersions and sterile powders for injection or dispersions. Examples of pharmaceutically acceptable carriers and excipients are discussed, e.g., in *Remington Pharmaceutical Science*, 16th Ed. Certain exemplary techniques and compositions for making dosage forms are described in the following references: *Modern Pharmaceutics*, Chapters 9 and 10, Banker & Rhodes, eds. (1979);

Lieberman et al., *Pharmaceutical Dosage Forms: Tablets* (1981); and Ansel, *Introduction to Pharmaceutical Dosage Forms*, 2nd Ed., (1976).

"Administering" refers to administration of agents as needed to achieve a desired effect. Exemplary routes of administration include, but are not limited to, oral, rectal, nasal, sublingual, buccal, intramuscular, subcutaneous, intravenous, intracisternal, transdermal, intrameningeal, and parenteral administration. Such administration can be, in certain embodiments, by injection, inhalation, or implant.

Suitably the route of administration and dosage form of the preparation are selected to maximize the effect of the treatment. Typical examples of the administration route include oral routes as well as parenteral routes, including intracerebral, intracisternal, intraperitoneal, intraoral, intrathecal, intrabronchial, intrarectal, subcutaneous, intramuscular and intravenous routes. However, the therapeutic agent for cancer, i.e., the inhibitors of at least one member of the SUMO conjugation pathway, is administered directly to a target site that is need of the treatment of a cancer. Specifically, the therapeutic agent can be administered to the target site by injection, catheter, incision or other suitable means. Typical examples of the dosage form include sprays, capsules, liposomes, tablets, granules, syrups, emulsions, suppositories, injections, ointments and tapes.

One skilled in the art can select an appropriate dosage and route of administration depending on the patient, the particular cancer being treated, the duration of the treatment, concurrent therapies, etc. In certain embodiments, a dosage is selected that balances the effectiveness with the potential side effects, considering the severity of the cancer.

For oral therapeutic administration, the composition may be combined with one or more carriers and used in the form of ingestible tablets, buccal tablets, troches, capsules, elixirs, suspensions, syrups, wafers, chewing gums, foods and the like. Such compositions and preparations should contain at least 0.1% of active compound. The percentage of the compositions and preparations may, of course, be varied and may conveniently be between about 0.1 to about 100% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring. The above listing is merely representative and one skilled in the art could envision other binders, excipients, sweetening agents and the like. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like.

The selected dosage level will depend upon a variety of factors including the activity of the particular compound employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

In general, the daily dose contains from about 0.1 mg to about 2000 mg of the active ingredient, or about 0.5 to about 60 mg of the active ingredient. This dosage form permits the full daily dosage to be administered in one or two oral doses. More than once daily or twice daily administrations, e.g., 3, 4, 5 or 6 administrations per day, are also contemplated herein.

The use of the terms "a" and "an" and "the" and similar referents in the context of the disclosure are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. All methods described herein can be performed in any suitable order unless otherwise indicated herein or otherwise clearly contradicted by context. The use of any and all examples, or exemplary language (e.g., "such as") provided herein, is intended merely to illustrate aspects and embodiments of the disclosure and does not limit the scope of the claims. The use of the term "and/or" and similar referents in the context of the disclosure is to be construed to cover the terms surrounding the "and/or" in combination and in the alternative. For example, "level of expression and/or conjugation" is to be construed to cover "level of expression" or "conjugation" or the combination "level of expression and conjugation," unless otherwise indicated herein or clearly contradicted by the context.

While the disclosure is detailed above in terms of a number of aspects and embodiments, variations of those aspects and embodiments may become apparent to those of ordinary skill in the art in light of the foregoing description. The examples that follow are intended merely to be illustrative of certain aspect and embodiments of the disclosure, and should not be interpreted to be limiting to the claims.

EXAMPLES

Materials and Methods

Tumor Sampling.

Informed patient consent was obtained according to the Helsinki declaration of ethical requirements, and consent also given by the local ethics committee at the University of Cologne/Germany (#03-170). Surgical specimens were obtained from 58 patients with astrocytoma tumors at the Department of Neurosurgery, University of Cologne, Germany. Tumor samples were taken during neurosurgery, snap-frozen in liquid nitrogen immediately after excision, and stored at −80° C. until analysis. All samples used for biochemical analyses were histologically evaluated using 10 μm cryostat sections stained with hematoxilin/eosin and compared with paraffin sections to guarantee that representative tissues were taken. Only those samples without evident necrosis were considered for analysis. Samples were classified according to the WHO malignancy scale into low-grade astrocytoma (WHO Grade II, AII), anaplastic astrocytoma (WHO Grade III, AIII), and glioblastoma multiforme (WHO Grade IV, GBM). 19 AII, 19 AIII and 20 GBM astrocytomas were used. Peritumoral white matter samples, where histological evaluation confirmed absence of tumor cells, served as controls.

Western Blot Analysis.

Frozen tumor samples were weighed in the cold and proteins extracted with lysis buffer composed of β-glycerophosphate (50 mmol/L; pH 7.4), 1 mmol/L EDTA, 1 mmol/L EGTA, 0.5 mmol/L $Na_3VO_4$, and 2% SDS to block desumoylation (i.e., deconjugation) of proteins. To further reduce the risk of de-sumoylation during protein extraction, frozen samples of about 20 mg were added to 10 volumes of lysis buffer, homogenized by a short sonication for 10 sec, and heated immediately afterwards to 95° C. for 10 min to heat-inactivate enzymes (Yang et al., *J. Cereb. Blood Flow Metabol.* 28: 269-279 (2008)). Protein concentration of extracts was analyzed using the BCA protein assay (Thermo Scientific), and identical amounts of proteins were loaded onto 4-16% gradient polyacrylamide gels (Biorad). Immunoblotting was performed using the following antibodies: SUMO1, SUMO2/3 (by courtesy of Dr. John Hallenbeck, NIH; Lee et al., *J. Cereb. Blood Flow Metabol.* 27: 950-962 (2007)), Ubc9 (BD Biosciences), and EGFR (Cell Signaling Technology) with β-actin (Sigma-Aldrich) as loading control. Image analysis was performed using the ImageJ program (Wayne Rasband, NIH).

Example 1

SUMO Conjugated Protein Levels in Glioblastoma Cells

Figure 1:
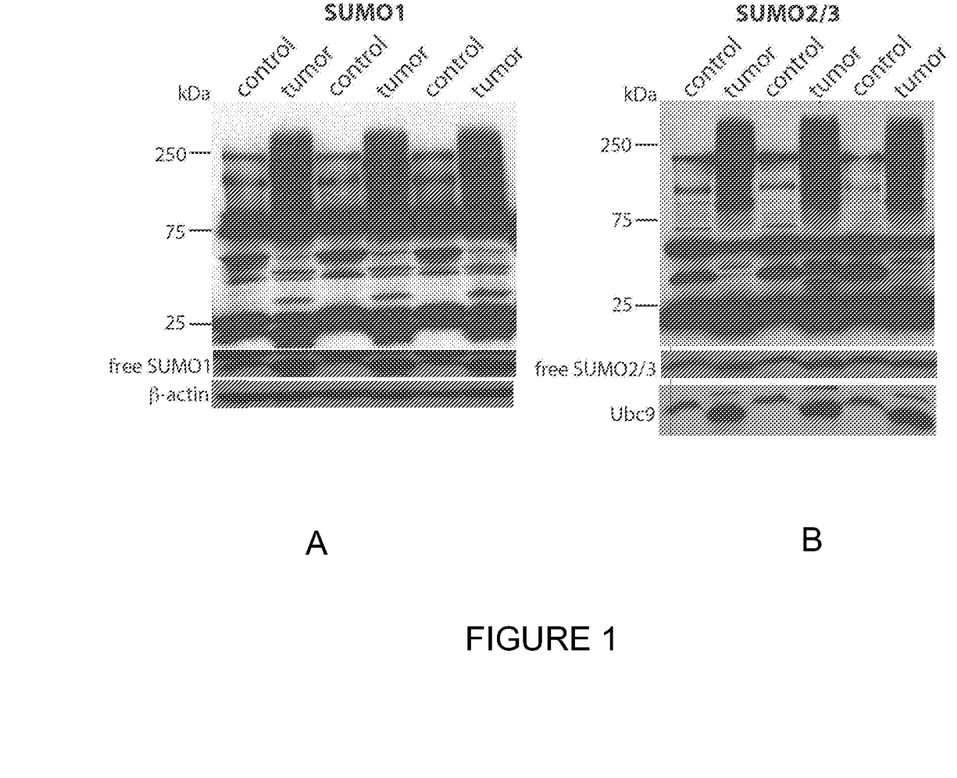
FIG. 1 shows a Western blot indicating the levels of SUMO1 conjugated protein (FIG. 1A) and SUMO2/3 conjugated proteins (FIG. 1B) and Ubc9 (FIG. 1B) in control brain and brain tumor tissues of rat.

To elucidate whether SUMO conjugation is activated in tumors, the brains of rats were inoculated with glioblastoma cells. Animals were anesthetized with isoflurane and mechanically ventilated. A 2 cm midline incision was made and the skull around the point of Bregma was exposed. A hole for the tumor cell injection was drilled at the coordinate AP 0 mm and L 2.5 mm from Bregma and 5 μl of tumor cell suspension (10,000 cells/5 μl) was slowly infused by a syringe pump over 5 min using a 30 gauge needle introduced into the striatum at a depth of 3.5 mm. Three weeks later, animals were reanesthetized with isoflurane and euthanized. Samples were taken from the tumor and the corresponding striatal tissue of the contralateral hemisphere. Proteins were extracted using lysis buffer supplemented with 2% SDS to block desumoylation. Protein extracts were loaded onto 4-16% PAGE gels. Western blot analysis showed the SUMO conjugation pathway was activated in the tumor tissue relative to the contralateral control tissue (FIG. 1). Levels of both SUMO1 (FIG. 1A) and SUMO2/3 (FIG. 1B) conjugated proteins were increased (smear of bands at high molecular weight above about 75 kDa).

In contrast to transient cerebral ischemia where activation of SUMO2/3 conjugation was associated with a decrease in amount of free SUMO2/3 and no change in the amount of the SUMO conjugating enzyme Ubc9 (Yang et al., *J. Cereb. Blood Flow Metabol.* 28: 269-279 (2008)), the amounts of Ubc9 protein and free SUMO1 and SUMO2/3 were much higher in the tumor tissue than in the contralateral control hemisphere (FIGS. 1A and 1B). This suggests that multiple components, or the entirety, of SUMO conjugation pathway is highly activated in tumor tissue.

Figure 2:
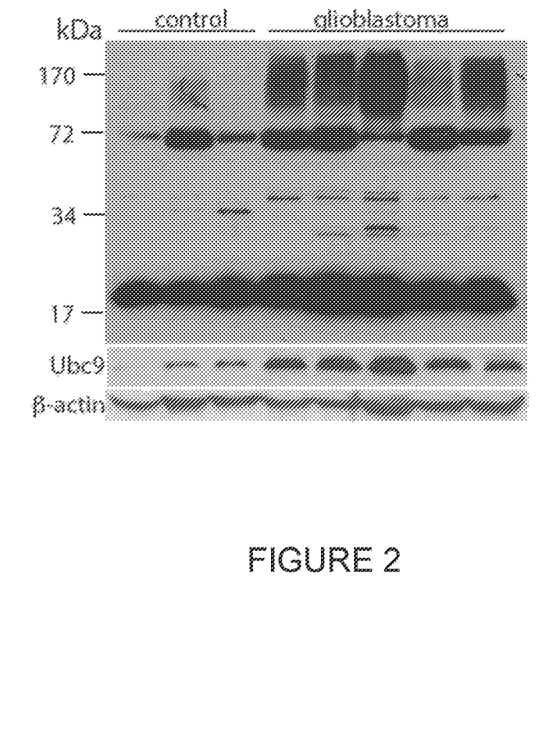
FIG. 2 shows a Western blot indicating the levels of SUMO2/3 conjugated proteins and Ubc9 in human control and glioblastoma tissue.

To verify whether these observations from experimental brain tumors in rats correlate to human brain tumors, SUMO conjugation was analyzed in tumor samples taken from human brains during neurosurgery as described above. Samples were taken from glioblastomas and from the surrounding brain tissue after verification that this tissue was histologically classified as being normal. As summarized in FIG. 2, human glioblastoma tissue exhibited activated (i.e., higher) levels of SUMO2/3 conjugated proteins (smear of bands at high molecular weight above about 75 kDa), and also higher levels of free SUMO2/3. Further similar to the observations in the rat model, protein levels of Ubc9 were increased in the human glioblastoma tissue.

Example 3

Characterization of Tumor Samples

Figure 3:
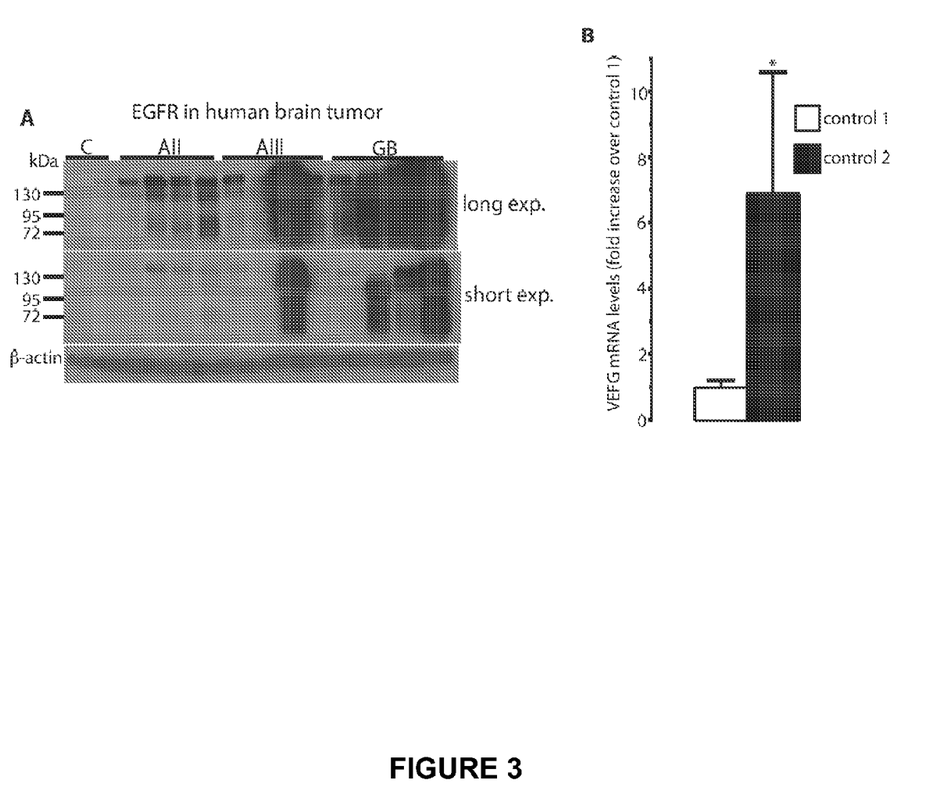
FIG. 3 shows a Western blot indicating the levels of EGFR protein in human control and tumor tissues (FIG. 3A) and a bar graph representing the normalized levels of VEGF mRNA in control samples (FIG. 3B).

Epidermal growth factor receptor (EGFR) has been shown to be amplified in GBM and to be associated with rapid tumor re-growth. (Malden et al., *Cancer Res.* 48: 2711-2714 (1988); Schlegel et al., *Int. J. Cancer.* 56: 72-77 (1994)). To evaluate whether the human astrocytoma specimens exhibited a pattern of EGFR amplification similar to that reported by other groups, EGFR protein levels were analyzed by Western blotting (FIG. 3A). Strong EGFR expression with various truncated forms was found in 47% of GBM samples and in one of the AIII samples (FIG. 3A), indicating that the samples are representative and comparable to those obtained by other groups (Schlegel et al., *Int. J. Cancer.* 56: 72-77 (1994)). Furthermore, the 170 kDa band of full-length EGFR appeared in almost all tumor samples, but at a much lower level.

Brain tumors induce peritumoral vasogenic brain edema, which may be associated with a decrease in ATP and increase in lactate levels, indicative of hypoxic conditions. Since prolonged hypoxia has been shown to activate the SUMO conjugation pathway, VEGF mRNA levels were evaluated in control samples derived from peritumoral white matter as a sensitive measure of hypoxic stress. Levels of VEGF and β-actin mRNA were evaluated by quantitative PCR. Total RNA was extracted from about 20 mg of frozen samples using the Trizol reagent (Invitrogen, Carlsbad). RNA was reversed transcribed into cDNA using random hexamers and oligo(dT) as primers (Invitrogen). PCR reactions were run in a Light-Cycler 2.0 (Roche Diagnostics). For quantification, changes in VEGF mRNA levels were related to β-actin mRNA levels. Data presented in FIG. 3B are mean values±standard deviation. Statistical analysis was performed using ANOVA and Fisher's PLSD test (* $p<0.05$ control1 versus control2). The levels of SUMO conjugated proteins in astrocytomas were normalized to levels in control samples exhibiting low VEGF mRNA levels (i.e., not hypoxic).

When normalized to β-actin mRNA levels, significantly higher VEGF mRNA levels were found in about 50% of control samples (6.3 (±3.9)-fold higher, $p<0.05$; FIG. 3B). This indicates that VEGF expression was activated by hypoxia in these samples, possibly through the peritumoral vasogenic brain edema associated with and triggered by brain tumors.

Example 4

SUMO Conjugation Pathway is Activated in Astrocytomas

Figure 4:
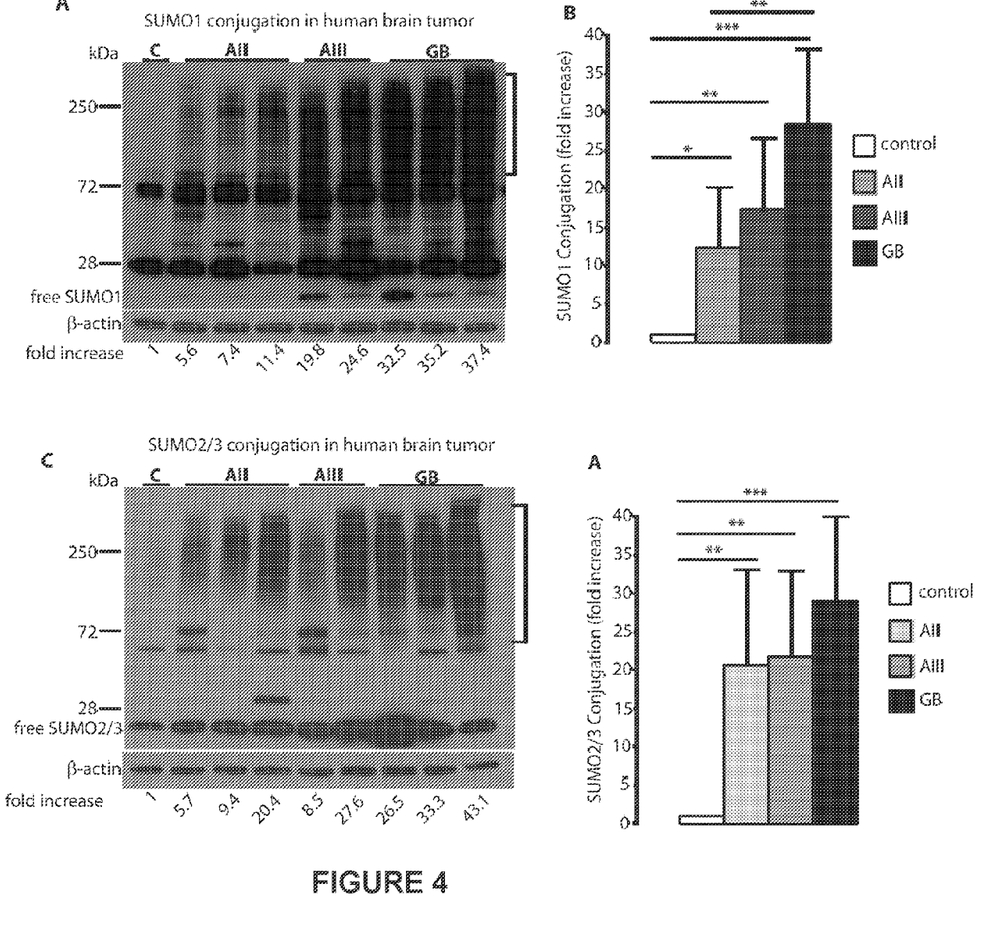
FIG. 4 shows Western blots indicating the levels of SUMO1 conjugated protein (FIG. 4A) and SUMO2/3 conjugated protein (FIG. 4C) in human control and tumor tissues and bar graphs representing the normalized levels of SUMO1 (FIG. 4B) and SUMO2/3 (FIG. 4D) depicted in FIGS. 4A and 4C, respectively.

Several hundred SUMO conjugated proteins have been identified in cell cultures exposed to stress conditions that activate the SUMO conjugation pathway (Bruderer et al., *EMBO Reports* 12: 142-148 (2011)). As such, a typical Western blot analysis has a large, strong smear of bands at a high molecular weight (Yang et al., *J. Cereb. Blood Flow Metabol.* 28: 892-896 (2008)). To quantify levels of SUMO conjugated proteins in tumors samples by Western blot analysis, a short exposure time was used with control samples so that the smear of bands representing SUMO conjugated proteins was barely visible (FIGS. 4A and 4C). For quantitative analysis, the high molecular weight area in each lane was cropped and analyzed. Data are presented as mean values±standard deviation (SD). Statistical analysis was performed using ANOVA and Fisher's PLSD test (* p<0.05;  p<0.01; * p<0.001).

Levels of SUMO1 conjugated proteins were increased in astrocytomas and exhibited an association based on tumor grade. Compared to control samples, levels of SUMO1 conjugated proteins were elevated 12.3 (±7.9)-fold, 17.4 (±9.2)-fold and 28.4 (±9.8)-fold in AII, AIII and GBM specimens, respectively (FIGS. 4A and 4B). While a trend appears to associate higher levels of SUMO1 conjugated proteins with an increased tumor malignancy grade, individual levels varied considerably, from 1.8- to 30.9-fold in AII, 5.8- to 39.1-fold in AIII, and 10.8 to 40.5-fold in GBM. Astrocytomas also exhibited high levels of SUMO2/3 conjugated proteins (FIG. 4C). Compared to control specimens, levels of SUMO2/3 conjugated proteins were 20.7 (±12.4)-fold, 21.8 (±11.1)-fold and (29.0)±10.9-fold elevated in AII, AIII and GBM samples, respectively (FIG. 4D).

Figure 5:
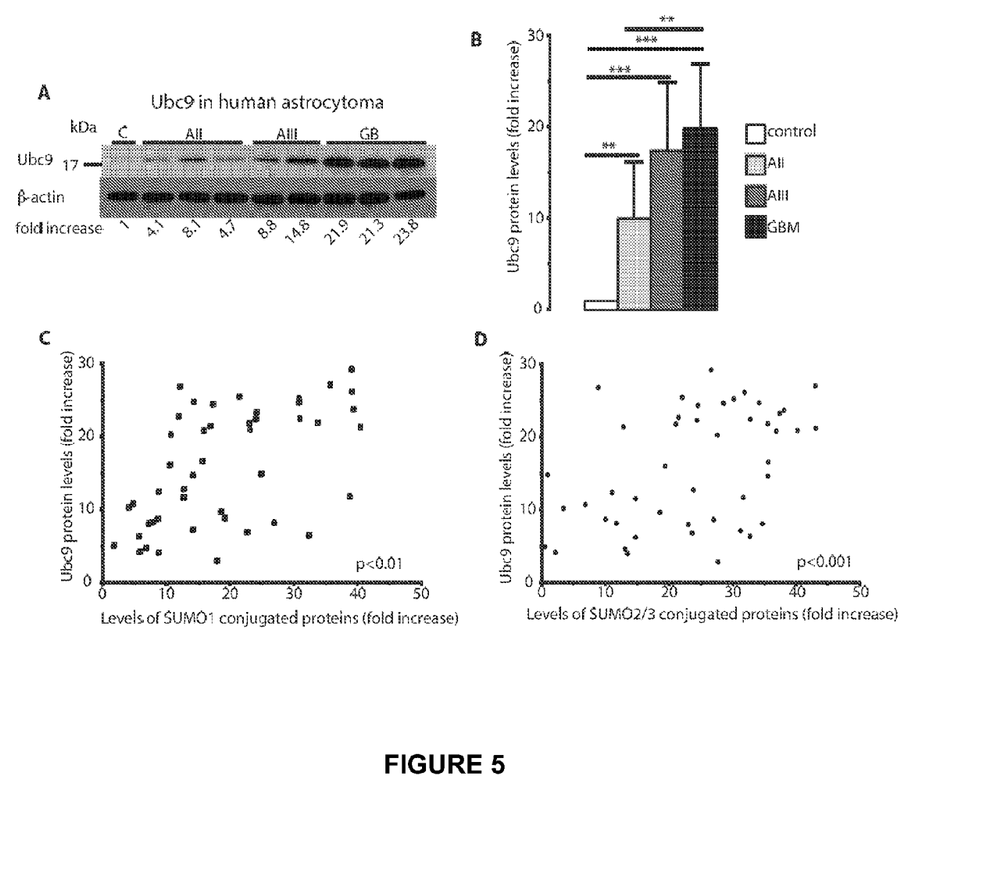
FIG. 5 shows a Western blot indicating the levels of the SUMO conjugating enzyme Ubc9 in human control and tumor tissue (FIG. 5A), a bar graph representing the normalized levels (FIG. 5B) and scatter plots showing the correlation between Ubc9 and SUMO1 (FIG. 5C) and SUMO2/3, respectively (FIG. 5D).

SUMO conjugation involves three enzymatic components including activating (E1), conjugating (E2) and ligating enzymes (E3). Ubc9 is the only E2 enzyme identified to date and its expression has been found to be increased in various malignant tissues including colon, prostate, breast, head and neck, and lung cancer, but decreased in metastatic breast, prostate and lung cancer. To evaluate the association of Ubc9 with SUMO conjugation, individual Ubc9 levels were related to the respective levels of SUMO1 (FIG. 5C) and SUMO2/3 (FIG. 5D) conjugated proteins. Statistical analysis was performed using Student's t-test for paired samples. Ubc9 protein levels were increased in astrocytoma samples, with a 10 (±6.2)-fold, 17 (±7.5)-fold and 20 (±7.1)-fold rise in AII, AIII and GBM, respectively (FIGS. 5A and 5B). Levels of SUMO1 (FIG. 4C) and SUMO2/3 (FIG. 5D) conjugated proteins were significantly related but not a perfect match to individual Ubc9 protein levels, suggesting that not only Ubc9 but other factors involved in the SUMO conjugation and deconjugation pathways contribute to the rise in levels of SUMO conjugated proteins seen here in the astrocytoma specimens.

Example 5

Silencing SUMO Expression Blocks DNA Synthesis

SUMO conjugation has been shown to play a role in DNA synthesis and DNA damage repair processes (Maxwell et al., Proc. Natl. Acad. Sci. USA 94: 8104-8109 (1997); Nguyen et al., Am. J. Pathol. 168: 1452-1463 (2006)). To investigate whether DNA synthesis of glioblastoma cells is modified by SUMO conjugation, the effects of suppressing SUMO conjugation on the incorporation of $^3$H-thymidine into DNA was evaluated. SUMO conjugation was suppressed by blocking its expression using a miRNA approach. To avoid the risk of adaptive processes taking place in cells where SUMO expression had been silenced during the long selection process for stably transfected cells, a 4-hydroxy tamoxifen (4-HT)-inducible lentiviral system was used to express designed miRNAs (Callus et al., Cell Death Diff. 15: 213-219 (2008)). Briefly, the 4-HT inducible lentiviral system utilizes two constructs and the UAS/GAL4 system. The ubiquitin promoter of the first construct drives expression of the GEV16 transcription factor that is retained in the cytoplasm in the absence of the induced 4-HT. In the presence of 4-HT, GEV16 translocates to the nucleus where the GAL4-DNA binding domain (UAS) directs binding to GAL4 upstream activating sequences located in the second construct, whereby transcription of the gene of interest is activated.

A miRNA-based RNAi vector expressing three pre-miRNAs against SUMO1 (target sequence: GGTCAGAGAATTGCTGATAAT (SEQ ID NO: 1)), SUMO2 (target sequence: GTTTGTCAATGAGGCAGATCA (SEQ ID NO: 2)) and SUMO3 (target sequence: AATCGAATCTGCCTCATTGAC (SEQ ID NO: 3)) was cloned into the vector pcDNA6.2-GW/EMGFP-miR (Invitrogen) by inserting miR-SUMO1 into the construct miR-SUMO2/3 (Yang & Paschen, Biochem. Biophys. Res. Commun. 382: 215-218 (2009)) using Bam I and Xho I restriction sites. One construct contained GFP and three pre-miRNAs against SUMO1, SUMO2 and SUMO3 (SUMO1/2/3-miR) and the other construct contained GFP and a control miRNA not related to any mammalian gene (Neg-miR) were generated by subcloning the fragment harboring GFP and miR-SUMO1/2/3 or miR-Neg into the vector pF5xUAS (Callus et al., Cell Death Diff. 15: 213-219 (2008)) to generate the constructs 5xUAS/miR-SUMO1/2/3 and 5xUAS/miR-Neg.

F98 rat glioblastoma cells (ATCC; CRL-2397) cultured in MEM medium were used for experiments. In order to generate 4-HT-inducible stable F98 cell lines, F98 cells were infected with GEV16 lentivirus and one of the two 5xUAS/miRNA constructs, 5xUAS/miR-Neg expressing miRNA not related to any mammalian gene to create control cells or 5xUAS/miR-SUMO1/2/3 expressing miRNA targeting SUMO1/2/3 to generate cells where SUMO1/2/3 expression is blocked by exposing cells to 4-HT, and selected with two antibiotics, hygromycin and puromycin. Single cell clones used in this study were selected by verifying GFP expression after induction with 100 nM 4-HT.

Figure 6:
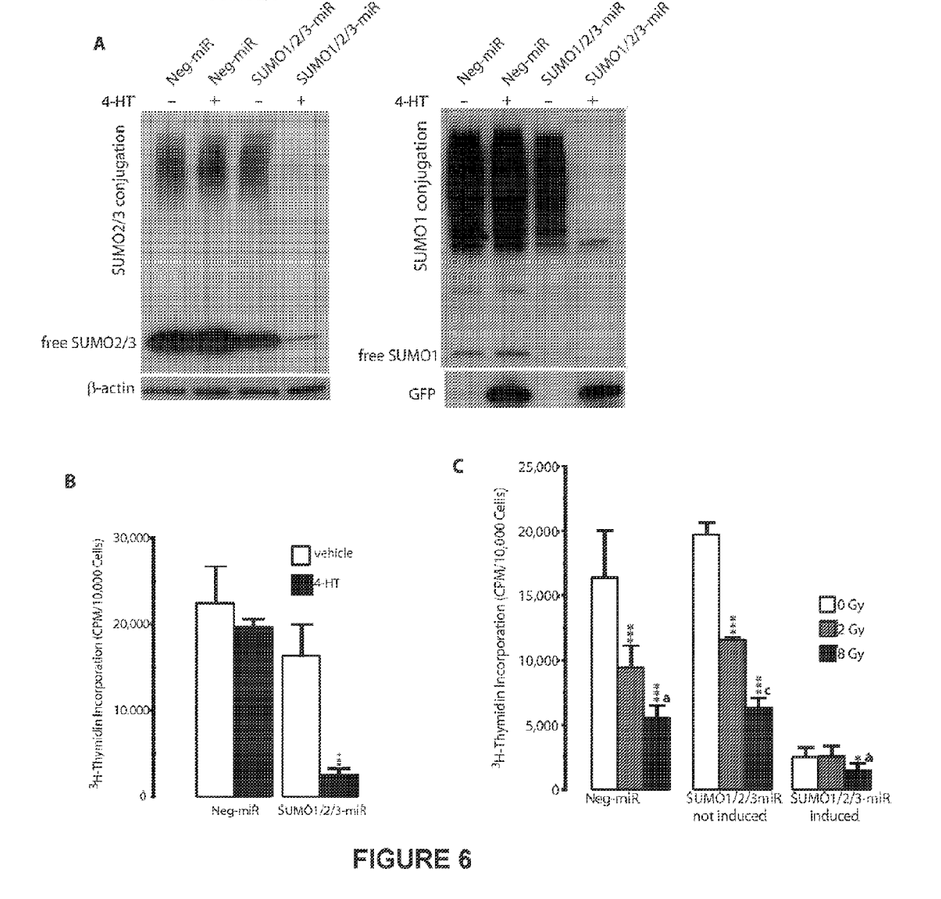
FIG. 6 shows a Western blot indicating the levels of SUMO2/3 conjugated protein and SUMO1 conjugated protein (FIG. 6A) in cells with or without SUMO1/2/3-miR induced or not induced with 4HT and a graph showing the effect of silencing SUMO expression, with or without radiation, on DNA synthesis (FIGS. 6B and 6C).

To verify the effects of 4-HT-induced activation of miRNA expression on levels of SUMO and SUMO conjugated proteins, stably transfected F98 cells were exposed to 100 nM 4-HT for 48 hr, and levels of SUMO1 and SUMO2/3 conjugated proteins were evaluated by Western blot analysis (FIG. 6A). Two days after adding 4-HT to cultures, SUMO1/2/3 expression was almost completely blocked in cells expressing SUMO1/2/3 miRNA (FIG. 6A). 4-HT exposure did not produce any major change in incorporation of $^3$H-thymidine into DNA in cells expressing the control miRNA (Neg-miR), but blocked $^3$H-thymidine incorporation in cells expressing SUMO1/2/3 miRNA (SUMO1/2/3-miR) to about 13% of control (FIG. 6B) and almost completely depleted levels of SUMO1 and SUMO2/3 conjugated proteins in cells expressing SUMO1/2/3 miRNA (FIG. 6A). This result illustrates the role of SUMO conjugation in DNA synthesis in glioblastoma cells.

The effect of SUMO1/2/3 miRNA expression on radiation induced impairment of DNA synthesis was investigated by measuring the uptake of $^3$H-thymidine. F98 cells were plated at a density of 20,000 cells/cm$^2$ in DMEM supplemented with 10% FBS (ATCC, Manassas Va.), 1% penicillin-streptomycin (Invitrogen), hygromycin B (10 μg/ml, Sigma Aldrich) and puromycin (5 μg/ml, Sigma-Aldrich) and grown at 37° C. in 5% $CO_2$ for 24 hr prior to the addition of 100 nM 4-HT or vehicle. Cells expressing control miRNA (Neg-miR) or SUMO1/2/3 (SUMO1/2/3-miR) miRNA with or without 4-HT induction for 2 days were exposed to radiation of various doses, i.e. 0, 2 or 8 Gy, at a rate of 142 cGy/min delivered at room temperature using an E1 Dorado Co-60 Irradiator. Irradiated cells were detached with trypsin-EDTA (Fisher Scientific), counted, re-suspended in culture medium with supplements described above, and re-plated in a 96-well plate at a density of 10,000 cells per well. 4-HT (100 nM) or vehicle was added and cells maintained for an additional 4 hr in 5% $CO_2$. $^3$H-thymidine (50 μCi, specific activity 46 Ci/mmol, ICN Biochemicals) was then added to the medium. Cells were harvested 24 hr later following detachment with trypsin-EDTA, collected on filter paper, dried overnight, and immersed in scintillation cocktail (ICN Biochemicals), and counted for 10 min in a liquid scintillation counter.

Four test conditions were examined: 1) Control miRNA cells+4-HT; 2) control miRNA cells+vehicle; 3) SUMO1/2/3 miRNA cells+4-HT; 4) SUMO1/2/3 miRNA cells+vehicle. Thymidine uptake for each test conditions/radiation dose was recorded in units of CPM per 10,000 cells as mean values of 6 replicate observations. Data shown in FIGS. 6B and 6C are presented as mean values±standard deviation. Statistical analysis was performed using ANOVA and Fisher's PLSD test (* $p<0.05$; *** $p<0.001$, for 4-HT versus vehicle (FIG. 6B) or 2 Gy or 8 Gy versus 0 Gy (FIG. 6C); a $p<0.05$, c $p<0.001$, 8 Gy versus 2 Gy).

Silencing SUMO1/2/3 expression by 4-HT-exposure suppressed $^3$H-thymidine incorporation in cells expressing SUMO1/2/3-miR but not in cells expressing Neg-miR (FIG. 6B), suggesting that SUMO conjugation plays a role in DNA synthesis. In cells expressing control miRNA, 2 or 8 Gy radiation reduced $^3$H-thymidine incorporation to 58% or 34% of control, respectively (FIG. 6C). Radiation produced a similar effect in cells transfected with the SUMO1/2/3 miRNA construct but not exposed to 4-HT, where $^3$H-thymidine uptake was reduced to 59% and 32% of control, respectively. This suggests that 4-HT exposure of cells did not modify $^3$H-thymidine incorporation. Upon 4-HT-induced silencing of SUMO1-3 expression, $^3$H-thymidine uptake was even further suppressed to 7.6% of control when cells were exposed to a radiation dose of 8 Gy (FIG. 6C), indicating that radiation and silencing of SUMO expression have an additive and/or synergistic inhibitory effect on $^3$H-thymidine incorporation.

Example 6

Silencing SUMO Expression and TMZ Toxicity

TMZ, an alkylating agent that damages DNA and triggers cell death, is frequently used as a drug in combination with surgical resection and radiation therapy to block GBM development. To investigate whether blocking SUMO conjugation by silencing its expression modifies TMZ toxicity, F98 glioblastoma cells expressing control or SUMO1/2/3 miRNA were exposed to various concentrations of TMZ and evaluated for the extent of cell death.

Figure 7:
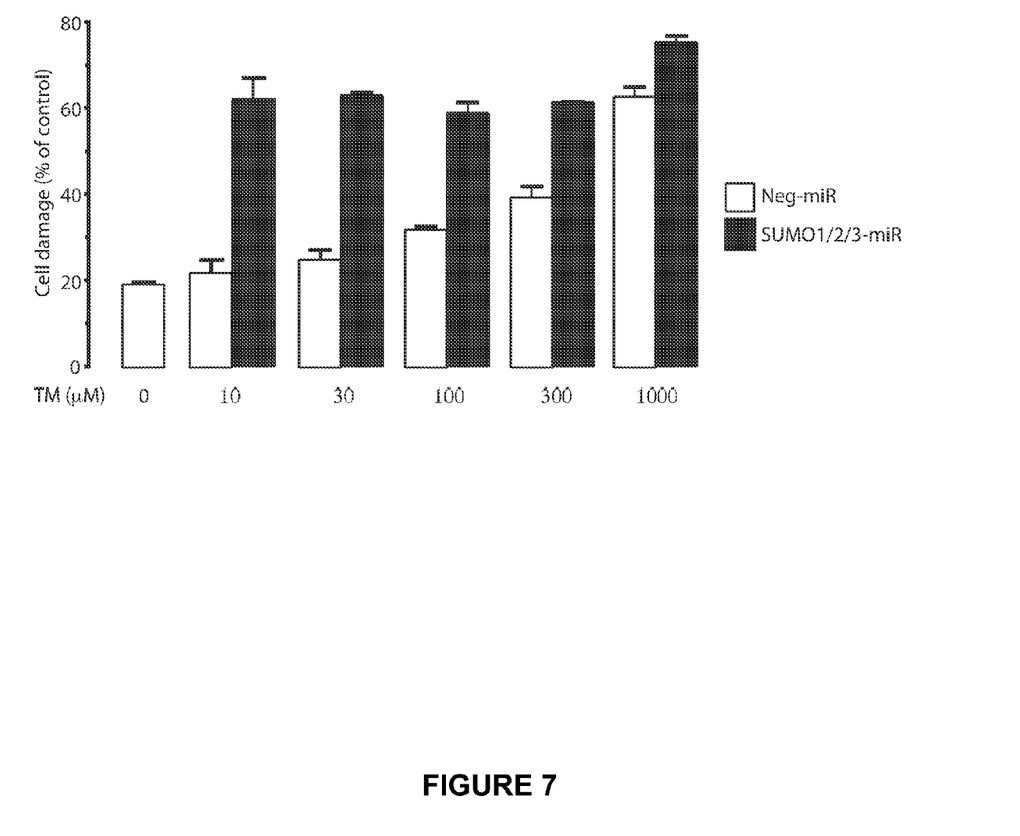
FIG. 7 shows a graph of cell damage of cells with or without SUMO1/2/3-miR which are treated with different amounts of TMZ.

F98 cells stably transfected with SUMO1/2/3-miR or Neg-miR constructs were exposed to 100 nM 4-HT for 2 days to silence SUMO expression and deplete endogenous SUMO1-3 (see FIG. 6A). The effect of miRNA expression on levels of SUMO1-3 conjugated proteins was verified by Western blotting. Cells were then detached with trypsin-EDTA, counted and re-plated in a 24-well plate at a density of 500,000 cells/well in medium supplemented with 100 nM 4-HT. The cells were exposed to 0, 10, 30, 100, 300 or 1000 µM TMZ for 72 hr. The extent of TMZ induced cell damage and cell death was evaluated by measuring the release of LDH from the cells into the medium (LDH Cytotoxicity Detection Kit, Clontech) in relation to total LDH activity (medium plus cells; expressed as percent of total LDH activity). TMZ exposure induced cell death in a concentration-dependent manner that was enhanced in cells where SUMO1/2/3 expression had been silenced. (FIG. 7).

What is claimed is:

1. A method of treating brain cancer in a subject in need of treatment, comprising: determining the level of conjugation of at least one member of the SUMO conjugation pathway in a sample from the subject; comparing the level of conjugation of the same member of the SUMO conjugation pathway in a control; and administering to the subject an effective amount of agent that causes levels of SUMO conjugated proteins to decrease if the sample has increased levels of conjugation of at least one member of the SUMO conjugation pathway relative to control cells, wherein the agent is an inhibitor of SUMO1, SUMO2 or SUMO3, wherein the inhibitor is an inhibitory RNA.

2. The method of claim 1, further comprising administering a second anti-cancer therapy to the subject.

3. The method of claim 2, wherein the second anti-cancer therapy is selected from an effective amount of a chemotherapy or radiation therapy.

4. The method of claim 3, wherein the chemotherapy comprises temozolomide (TMZ).

5. The method of claim 1, wherein the at least one member of the SUMO conjugation pathway is Ubc9, SUMO1, SUMO2 or SUMO3.

6. The method of claim 1, wherein the brain cancer is sarcoma, carcinoma, lymphoma, glioblastoma, or astrocytoma.

7. The method of claim 1, wherein the brain cancer is an astrocytoma of grade I, grade II, grade III or grade IV.

8. The method of claim 1, wherein the inhibitory RNA is a dsRNA, a siRNA, a piRNA, an antisense RNA, a RNAse external guide sequence, a miRNA, a ribozyme, or a shRNA comprising a sequence complementary to a portion of an RNA sequence encoding SUMO1, SUMO2 or SUMO3.

9. The method of claim 8, wherein the inhibitory RNA comprises a miRNA comprising a sequence complementary to a sequence of SUMO1, SUMO2, or SUMO3, or any combination thereof.

10. A method of reducing proliferation of a brain cancer cell comprising: determining the level of conjugation of at least one member of the SUMO conjugation pathway in the brain cancer cell; comparing the level of conjugation of the same member of the SUMO conjugation pathway in a control; and contacting the brain cancer cell with an agent that causes levels of SUMO conjugated proteins to decrease in an amount effective to reduce proliferation if the brain cancer cell has increased levels of conjugation of at least one member of the SUMO conjugation pathway relative to a control cell, wherein the agent is an inhibitor of SUMO1, SUMO2 or SUMO3, wherein the inhibitor is an inhibitory RNA.

11. A method of promoting differentiation of a brain cancer cell comprising: determining the level of conjugation of at least one member of the SUMO conjugation pathway in the brain cancer cell; comparing the level of conjugation of the same member of the SUMO conjugation pathway in a control cell; and contacting the brain cancer cell with an agent that causes levels of SUMO conjugated proteins to decrease in an amount effective to increase differentiation if the brain cancer cell has increased levels of conjugation of at least one member of the SUMO conjugation pathway relative to a control cell, wherein the agent is an inhibitor of SUMO1, SUMO2 or SUMO3, wherein the inhibitor is an inhibitory RNA.

12. A method of inhibiting the survival of a brain cancer cell comprising: determining the level of conjugation of at least one member of the SUMO conjugation pathway in the brain cancer cell; comparing the level of conjugation of the same member of the SUMO conjugation pathway in a control cell; and contacting the brain cancer cell with an effective amount of an agent that causes levels of SUMO conjugated proteins to decrease in an amount effective to inhibit survival of the brain cancer cell, if the sample has increased levels of conjugation of at least one member of the SUMO conjugation pathway relative to a control cell, wherein the agent is an inhibitor of SUMO1, SUMO2 or SUMO3, wherein the inhibitor is an inhibitory RNA.

13. The method of claim 12, further comprising contacting the brain cancer cell with an anti-cancer agent selected from a chemotherapeutic and radiation.

14. The method of claim 13, wherein the chemotherapeutic comprises TMZ.

15. A method of inhibiting DNA synthesis in a brain cancer cell comprising: determining the level of conjugation of at least one member of the SUMO conjugation pathway in the brain cancer cell; comparing the level of conjugation of the same member of the SUMO conjugation pathway in a control cell; and contacting the brain cancer cell with an amount of an agent that causes levels of SUMO conjugated proteins to decrease and an amount of TMZ or radiation effective to inhibit DNA synthesis if the brain cancer cell has increased levels of conjugation of at least one member of the SUMO conjugation pathway relative to a control cell, wherein the agent is an inhibitor of SUMO1, SUMO2 or SUMO3, wherein the inhibitor is an inhibitory RNA.

16. A method of inducing cell death in a brain cancer cell comprising: determining the level of conjugation of at least one member of the SUMO conjugation pathway in the brain cancer cell; comparing the level of conjugation, of the same member of the SUMO conjugation pathway in a control cell; contacting the brain cancer cell with a combination of an amount of an agent that causes levels of SUMO conjugated proteins to decrease and an amount of TMZ or radiation effective to induce cell death if the brain cancer cell has increased levels of conjugation of at least one member of the SUMO conjugation pathway relative to a control cell, wherein the agent is an inhibitor of SUMO1, SUMO2 or SUMO3, wherein the inhibitor is an inhibitory RNA.

17. The method of claim 1, wherein the increased level of conjugation of the member of the SUMO conjugation pathway is indicated by an increase in the amount of conjugated SUMO1, SUMO2 or SUMO3.

18. The method of claim 1, wherein the sample is selected from blood, cerebrospinal fluid, urine, saliva, a tissue biopsy, and tumor cells.

* * * * *

SEQUENCE LISTING

```
<160> NUMBER OF SEQ ID NOS: 3

<210> SEQ ID NO 1
<211> LENGTH: 21
<212> TYPE: DNA
<213> ORGANISM: Artificial Sequence
<220> FEATURE:
<223> OTHER INFORMATION: Synthetic

<400> SEQUENCE: 1
ggtcagagaa ttgctgataa t                                            21

<210> SEQ ID NO 2
<211> LENGTH: 21
<212> TYPE: DNA
<213> ORGANISM: Artificial Sequence
<220> FEATURE:
<223> OTHER INFORMATION: Synthetic

<400> SEQUENCE: 2
gtttgtcaat gaggcagatc a                                            21

<210> SEQ ID NO 3
<211> LENGTH: 21
<212> TYPE: DNA
<213> ORGANISM: Artificial Sequence
<220> FEATURE:
<223> OTHER INFORMATION: Synthetic

<400> SEQUENCE: 3
aatcgaatct gcctcattga c                                            21
```